United States Patent
Yang et al.

(10) Patent No.: US 9,228,431 B2
(45) Date of Patent: Jan. 5, 2016

(54) FREQUENCY LOCATION APPARATUS, METHODS, AND SYSTEMS

(71) Applicant: Halliburton Energy Services, Inc., Houston, TX (US)

(72) Inventors: Jie Yang, Paoli, PA (US); Rebecca Corina Jachmann, Kingwood, TX (US)

(73) Assignee: Halliburton Energy Services, Inc, Houston, TX (US)

( * ) Notice: Subject to any disclaimer, the term of this patent is extended or adjusted under 35 U.S.C. 154(b) by 0 days.

(21) Appl. No.: 14/423,811

(22) PCT Filed: Oct. 4, 2012

(86) PCT No.: PCT/US2012/058750
§ 371 (c)(1),
(2) Date: Feb. 25, 2015

(87) PCT Pub. No.: WO2014/055080
PCT Pub. Date: Apr. 10, 2014

(65) Prior Publication Data
US 2015/0204186 A1     Jul. 23, 2015

(51) Int. Cl.
*G01V 3/00* (2006.01)
*E21B 47/12* (2012.01)
*G01N 24/08* (2006.01)
*G01V 3/32* (2006.01)

(52) U.S. Cl.
CPC ............ *E21B 47/122* (2013.01); *G01N 24/081* (2013.01); *G01V 3/32* (2013.01)

(58) Field of Classification Search
USPC ....................................................... 340/855.4
See application file for complete search history.

(56) References Cited

U.S. PATENT DOCUMENTS

| | | |
|---|---|---|
| 4,639,671 A | 1/1987 | Macovski |
| 4,806,866 A | 2/1989 | Maier |
| 4,894,616 A * | 1/1990 | Yoshitome ......... G01R 33/4838 324/309 |
| 5,001,428 A | 3/1991 | Maier |
| 5,327,086 A | 7/1994 | Bodenhausen et al. |
| 5,451,873 A | 9/1995 | Freedman et al. |
| 5,912,558 A | 6/1999 | Halamek |

(Continued)

FOREIGN PATENT DOCUMENTS

| | | |
|---|---|---|
| GB | 1448939 A | 9/1976 |
| WO | WO-2011/119528 A2 | 9/2011 |
| WO | WO-2014055080 A1 | 4/2014 |

OTHER PUBLICATIONS

"Australian Application Serial No. 2012391497, First Examiner Report mailed Apr. 30. 2015", 3 pgs.

(Continued)

*Primary Examiner* — Naomi Small
(74) *Attorney, Agent, or Firm* — Schwegman Lundberg & Woessner, P.A.; Benjamin Fite

(57) ABSTRACT

In some embodiments, an ex-situ apparatus and a system, as well as a method and an article, operate to transmit wideband modulated pulses to generate an externally-projected oscillating magnetic field in a material body, to record one or more raw echo free induction decay (REFID) signals during echo acquisition periods following some of the second modulated pulses, and to transform the acquired REFID signals via frequency decomposition to determine a preferred nuclear magnetic resonance frequency associated with a maximum amplitude of decomposed frequency components. Additional apparatus, systems, and methods are described.

22 Claims, 7 Drawing Sheets

(56) References Cited

U.S. PATENT DOCUMENTS

| | | |
|---|---|---|
| 6,573,716 B2 | 6/2003 | Toufaily et al. |
| 6,600,316 B2 | 7/2003 | Chen et al. |
| 6,717,404 B2 | 4/2004 | Prammer |
| 7,026,814 B2 | 4/2006 | Bordon et al. |
| 7,084,635 B2 | 8/2006 | Morita et al. |
| 7,539,279 B2 | 5/2009 | Lu et al. |
| 8,004,279 B2 | 8/2011 | Kruspe et al. |
| 2004/0263164 A1 | 12/2004 | Kurimoto et al. |
| 2005/0156592 A1 | 7/2005 | Bordon et al. |
| 2007/0032956 A1 | 2/2007 | Blanz et al. |
| 2007/0140546 A1* | 6/2007 | Suh .................. G01N 27/9046 382/141 |
| 2007/0279058 A1* | 12/2007 | Bulkes ............... G01R 33/3614 324/314 |
| 2010/0076693 A1* | 3/2010 | Liang ................ G06K 9/00516 702/22 |
| 2010/0271019 A1* | 10/2010 | Anand ................ G01N 24/081 324/303 |
| 2011/0227570 A1 | 9/2011 | Anand et al. |
| 2012/0001629 A1 | 1/2012 | Hopper et al. |

OTHER PUBLICATIONS

"European Application Serial No. 12885984.0, Extended European Search Report mailed Jul. 1, 2015", 8 pgs.

Mitchell, J., et al., "A rapid measurement of T1/T2T1/T2: The DECPMG sequence", *Journal of Magnetic Resonance*, 200(2), (Oct. 2009), 198-206.

Prammer, M. G., et al., "A New Multiband Generation of NMR Logging Tools", SPE-49011-MS, *SPE Annual Technical Conference and Exhibition*, Sep. 27-30, New Orleans, Louisiana, (1998), 1-7.

"International Application Serial No. PCT/US2012/058750, International Preliminary Report on Patentability mailed Nov. 14, 2014", 4 pgs.

"International Application Serial No. PCT/US2012/058750, International Search Report mailed Dec. 14, 2012", 2 pgs.

"International Application Serial No. PCT/US2012/058750, Written Opinion mailed Dec. 14, 2012", 7 pgs.

\* cited by examiner

FREQUENCY LOCATION APPARATUS, METHODS, AND SYSTEMS

PRIORITY APPLICATIONS

This application is a U.S. National Stage Filing under 35 U.S.C. 371 from International Application No. PCT/US2012/058750, filed on 4 Oct. 2012, and published as WO 2014/055080 on 10 Apr. 2014, which application and publication are incorporated herein by reference in their entirety.

BACKGROUND

Understanding the structure and properties of geological formations can reduce the cost of drilling wells for oil and gas exploration. Measurements made in a borehole (i.e., down hole measurements) are typically performed to attain this understanding, to identify the composition and distribution of material that surrounds the measurement device down hole. To obtain such measurements, a variety of sensors are used, including nuclear magnetic resonance (NMR) sensor probes. When used down hole, in conjunction with a magnet and drive electronics, measurements made by the NMR sensor probe can be used to provide information about the surrounding formation.

Generally, a permanent magnet's remnant field strength ($B_O$) is a function of temperature. Thus, when magnets are used in locations where temperatures vary widely, such as down hole, the preferred NMR activation frequency (which gives the best signal strength) may change with temperature. Searching to locate the preferred NMR frequency at any given temperature can be time-consuming.

DETAILED DESCRIPTION

To address some of the challenges described above, as well as others, apparatus, systems, and methods are described herein that employ a searching mechanism to determine the preferred NMR frequency at any given temperature relatively quickly, when compared to conventional methods. This mechanism lends itself to use in the laboratory, as well as down hole.

Thus it should be noted that while many embodiments of the invention are described herein with respect to ex-situ use in a geological formation, this has been done for reasons of simplicity and clarity. Any of the embodiments described herein may be used ex-situ to determine the characteristics of a wide variety of material bodies in a variety of environments, outdoors or indoors, including laboratories. As used herein, a "material body" means any composition of matter that has a substantial (solid or liquid) character. Thus, a material body includes a geological formation, human tissue, component assemblies, a fiber composite, water in a tank, glycerol, oil, etc. Various example embodiments that can provide some or all of these advantages will now be described in detail.

Figure 1:
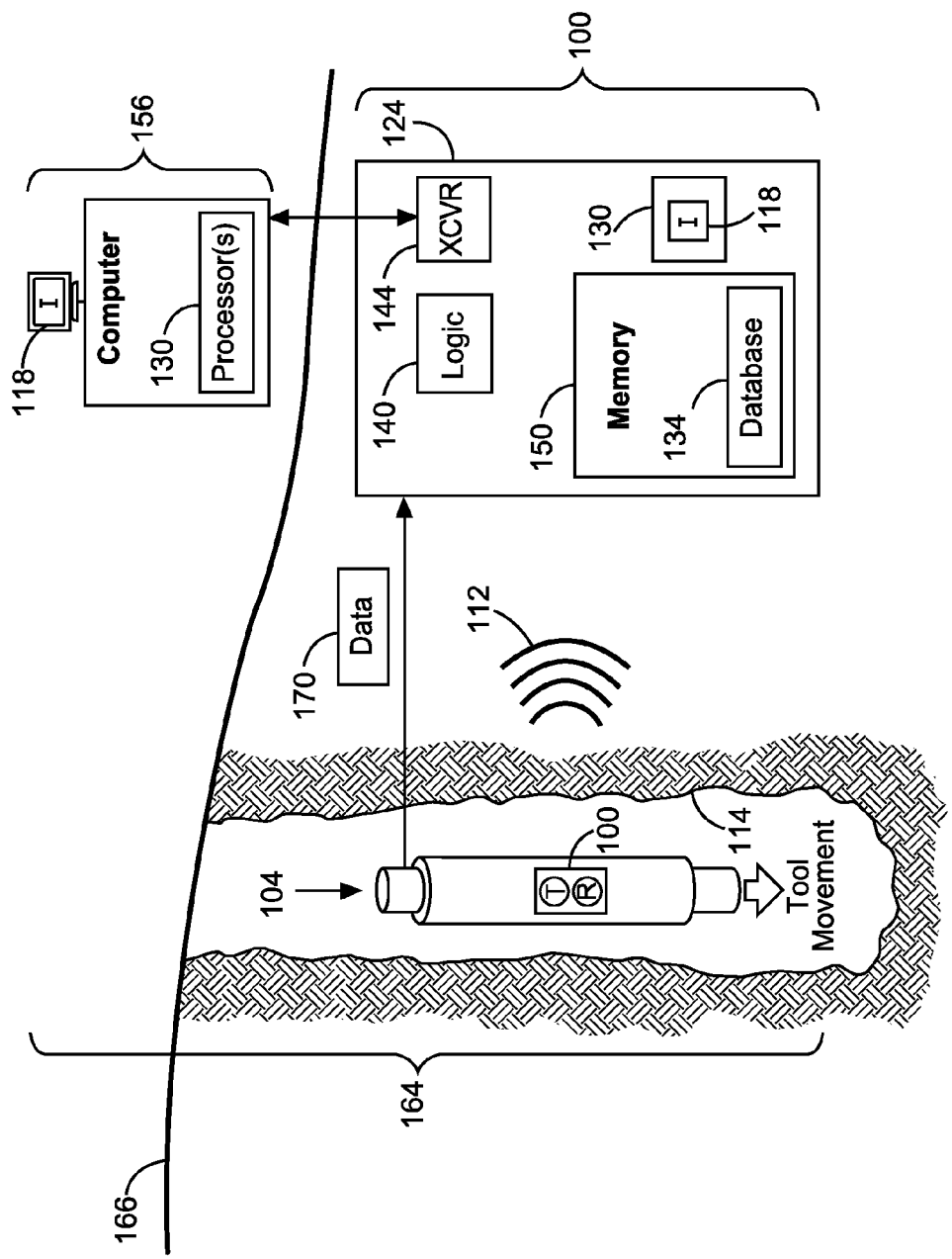
FIG. 1 is a block diagram of ex-situ apparatus and systems according to various embodiments of the invention.

FIG. 1 is a block diagram of ex-situ apparatus 100 and systems 164 according to various embodiments of the invention. In some embodiments, the system 164 comprises one or more of the apparatus 100, which may include a housing 104.

Processor(s) 130 that form part of the apparatus 100 may be located at the surface 166, as part of a surface logging facility 156, or in a data acquisition system 124 above or below the Earth's surface 166. In some embodiments, one or more processors 130 are packaged with the apparatus 100, and attached to the housing 104. As used herein, the term "attached" can refer to direct attachment (where one component is physically coupled to another, without an intervening element), or indirect attachment (where one component is physically coupled to another, via at least one other intervening element). The system 164 may comprise a data transceiver 144 (e.g., a telemetry transmitter and/or receiver) to transmit acquired data 170 provided by one or more electromagnetic transmitter and receiver pairs, and a magnet, forming part of the apparatus 100.

Logic 140 can be used to acquire and process the data 170 received from sensors forming part of the apparatus 100, according to the various methods described herein. For example, the logic 140 may comprise filters, such as quadrature filters, to filter the data 170. Received data and filtered data can be stored in the memory 150, perhaps as part of a database 134. Images 118 may be generated from the data 170 by the processors 130, and stored in the memory 150 or sent to the surface logging facility 156 for storage and/or display. Thus, many embodiments may be realized.

For example, an apparatus 100 may comprise one or more electromagnetic transmitter and receiver pairs (T,R) attached to a housing 104, such as a down hole tool, as well as one or more processors 130 attached to the down hole tool. A series of externally pulsed projected oscillating magnetic fields 112 are generated, via turning the transmitter T on and off.

In a geological formation 114, or in any other material body (e.g., a human body, a fiberglass composite aircraft wing, etc.), a variety of pulse types, such as wide band, frequency modulated pulses, and/or chirp pulses, (wide band phase modulated pulses), can be used to create the fields 112. In between pulses, the processors 130 can be used to record raw echo free induction decay (REFID) signals provided by the receiver R. For example, the REFID signals may be present during an echo acquisition period that follows each one of a series of modulated pulses forming part of a pulse train transmitted by the transmitter T. For the purposes of this document, the reader should note that the REFID signal described herein is different from the integrated result of a quadrature-detected signal.

The processor(s) 130 can be used to transform the recorded REFID signals via frequency decomposition to determine a preferred nuclear magnetic resonance (NMR) frequency for at least one of the transmitter and receiver pairs (T,R) at the ambient temperature, which is the temperature surrounding the apparatus 100. Maintaining a record of temperature versus frequency can be useful, since this may prevent having to repeat a calibration sequence, and may also be used to show that a tool is in the same working condition as it was previously. The details of pulse sequences forming pulse trains to be sent by the transmitter T, and the processing of associated REFID signals acquired by the receiver R (used to determine the preferred NMR frequency for the transmitter/receiver pair T,R), will now be described.

Figure 2:
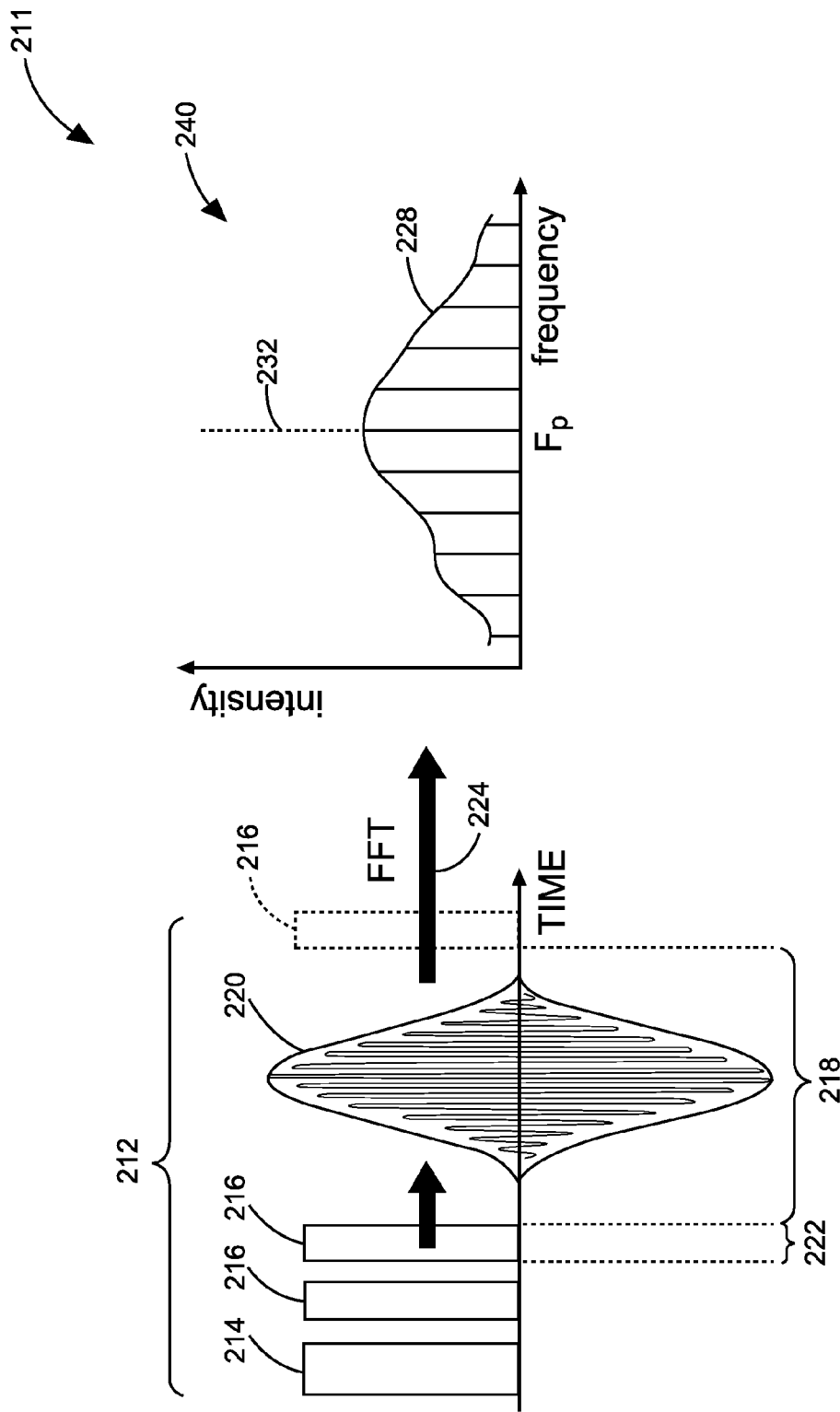
FIG. 2 illustrates an ex-situ process by which the preferred NMR frequency can be found, according to various embodiments of the invention.

FIG. 2 illustrates an ex-situ process 211 by which the preferred NMR frequency 232 can be found, according to various embodiments of the invention. The process 211 can be used in a wide variety of environments, over a wide variety of ambient temperatures, and may be applied to a number of configurations of the apparatus 100 and system 164 shown in FIG. 1.

To begin the process 211, a transmitter provides a train 212 of pulses, including a first pulse 214 and one or more second pulses 216. The first pulse may be a $\pi/2$ radio frequency (RF) pulse. The second pulse(s) 216 may be $\pi$ RF pulses.

The terms "$\pi$ RF pulse" and "$\pi/2$ RF pulse" are used herein according to their conventional meaning. That is, a $\pi$ RF pulse is an NMR transmission pulse that causes the absolute value of the tip angle of the magnetization vector with respect to the Z axis to be equal to $\pi$ radians. A $\pi/2$ RF pulse is an NMR transmission pulse that causes the absolute value of the tip angle of the magnetization vector with respect to the Z axis to be equal to $\pi/2$ radians.

In some embodiments, the acquisition of the REFID signal 220 occurs immediately after the first pulse 214 in the train 212, as well as after one or more of the second pulses 216 in the train 212. The time period that begins at the start of each pulse in the train 212, and that ends at the beginning of the next pulse in the train, comprises a pulse window time frame 222 (e.g., the time occupied by one pulse 216) and its associated echo acquisition period 218). The sum of the pulse window time frame 222 and the echo acquisition period 218 constitute a pulse-echo time frame. In some embodiments, the train 212 comprises only one first pulse 214 and one second pulse 216.

The pulse trains 212 provided by the transmitter can occur anywhere along a continuum of frequencies, with each pulse having a bandwidth of greater than or equal to 3% of the center transmit frequency of the pulse. For example, individual pulses in the train 212 might have a center transmit frequency of about 100 kHz to about 2 MHz, with a bandwidth of at least 3 kHz. In some embodiments, the bandwidth of the pulses in the train 212 may be increased in subsequent trains, such as when the initial band of acquisition appears to be far from the desired signal. In another example, several transmission pulse trains 212 might be utilized where the center frequency of the transmission pulse is incremented, for example by 10 kHz, between the trains 212, with a pulse 216 bandwidth of at least 13.5 kHz, over an incremented frequency range of about 450 kHz to about 550 kHz. In another embodiment, each pulse 216 in a single train 212 might have its center transmit frequency incremented by 10 kHz.

The REFID signal 220 obtained by the receiver, and provided to acquisition electronics (e.g., a data acquisition system, logic, and/or a processor) during one or more of the echo acquisition periods 218 that follows each of the pulses 214, 216 provided by the transmitter in the train 212, can be transformed via frequency decomposition to provide a spectrum of decomposed frequency components 228. The transformation 224 may take the form of a fast Fourier transform (FFT), to provide the decomposed frequency components 228. Filters, such as quadrature filters, can be applied to the REFID signal 220 to generate the decomposed frequency components 228 directly.

As seen in the graph 240, the preferred NMR frequency 232 for a particular location (e.g., a laboratory or down hole in a formation) and temperature can be selected from the decomposed frequency components 228 as the frequency which has a maximum amplitude value. Whether the decomposed frequency components 228 comprise a set of continuous or discrete frequencies, the preferred NMR frequency 232 can be chosen in the same way. In most embodiments, the preferred NMR frequency 232 turns out to be selected from one of many frequencies, as the signal which results in a received REFID signal 220 that has the greatest received signal-to-noise ratio (SNR). Multiple REFID signals 220 can be averaged, or the decomposed frequency components 228 can be averaged, to improve the accuracy of selecting the preferred NMR frequency 232.

The magnetic field of an in-situ instrument is substantially singular in strength, such that in-situ instruments are commonly said to have a single Larmor Frequency available, but a search must still be conducted to find it. When this frequency is not used for NMR signal acquisition, a substantial amount of received signal is lost. In the ex-situ apparatus and systems described herein (e.g., see FIGS. 1 and 3-5), a continuum of Larmor frequencies exist. Any of these ex-situ Larmor frequencies can be used in the pulses 214, 216 to obtain REFID signals 220, but some transmit frequencies will provide a much better return signal level than others. The transmitted pulse frequency at which the best return signal results is designated herein as the "preferred" NMR frequency 232 among a continuum of Larmor frequencies that provides the maximum amplitude among the decomposed frequency components 228.

Those of ordinary skill in the art will realize, after reading this disclosure and the attached figures, that the process 211 can be accomplished using analog, digital, and/or combinations of these types of electronics. Several such embodiments will now be described.

Figure 3:
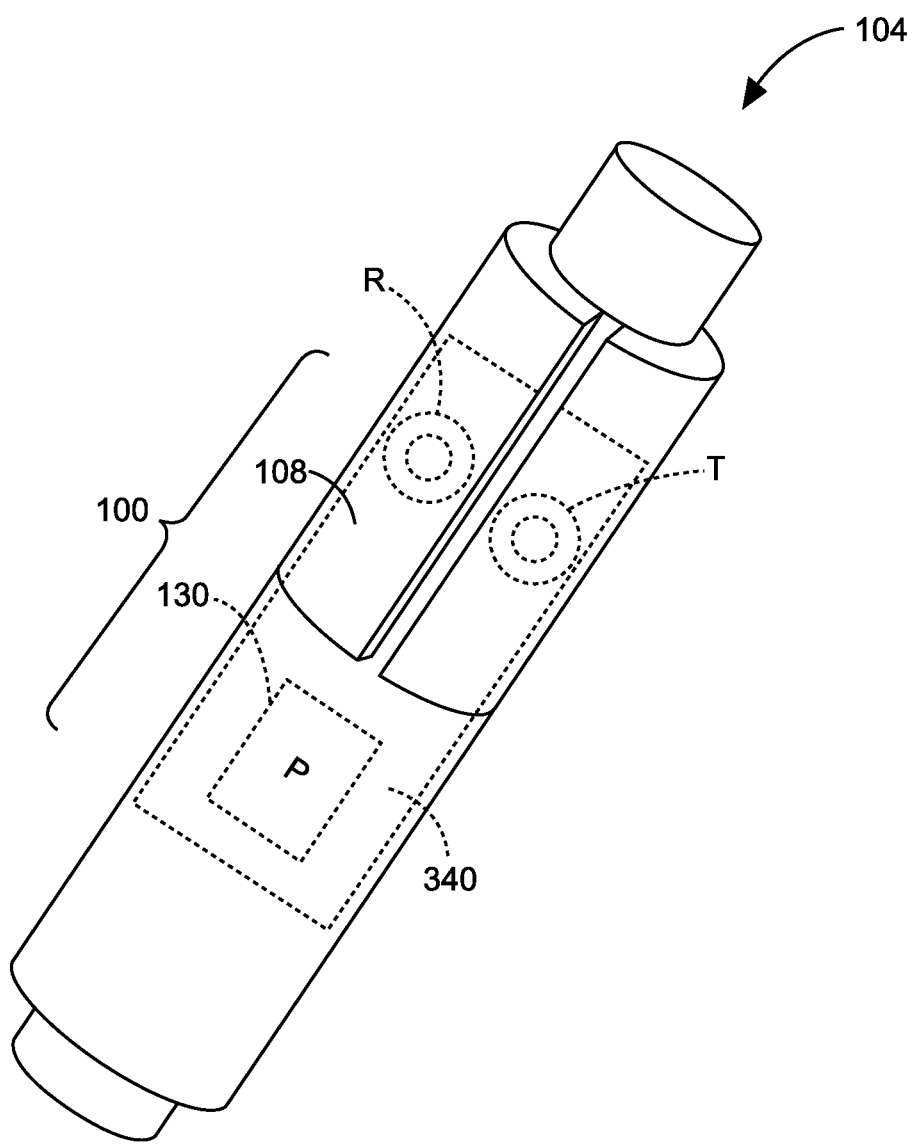
FIG. 3 illustrates a perspective view of a housing comprising a down hole tool attached to an apparatus according to various embodiments of the invention.

FIG. 3 illustrates a perspective view of a housing 104 comprising a down hole tool attached to an apparatus 100 according to various embodiments of the invention. Here the apparatus 100 is shown to comprise at least one electromagnetic transmitter T and receiver R pair, as well as a magnet 108. The apparatus 100 also comprises one or more processors 130. The processors 130 can be used to locate the preferred NMR frequency for the electromagnetic transmitter T and receiver R pair, as well as to acquire NMR data, from which formation images 118 (see FIG. 1) and other information about the formation can be derived, including formation permeability values.

Thus, referring now to FIGS. 1-3, it can be seen that many embodiments may be realized, including an ex-situ apparatus 100 that comprises at least one electromagnetic transmitter and receiver pair (T,R) and one or more processors 130 to record one or more REFID signals 220 provided by the receiver R. The REFID signals 220 can be recorded during echo acquisition periods 218 that follow the first and second pulses 214, 216, respectively. The pulses 214, 216 may be modulated, using a variety of techniques.

In many embodiments, the pulse train 212 comprises a first modulated pulse 214 followed by a series of second modulated pulses 216. The pulse train 212 is used to generate pulsed externally-projected oscillating magnetic fields 112 in a geological formation 114, or in any other material body. In many embodiments, the first and/or second modulated pulses 214, 216 have a bandwidth that is greater than three percent of their center transmit frequency. After the REFID signals 220 have been acquired, the processors 130 can be used to transform the REFID signals 220 via frequency decomposition into decomposed frequency components 228, perhaps using an FFT. Decomposition permits determining a preferred NMR frequency 232 for one or more of the electromagnetic transmitter and receiver pairs (T,R) as a frequency associated with one of the decomposed frequency components 228 that has the maximum amplitude.

In some embodiments, the components of the apparatus 100 are assembled together, into a single unit. Thus, the apparatus 100 may be configured so that one or more of the electromagnetic transmitter and receiver pairs (T, R), and the processor(s) 130, are attached to a common chassis 340 (e.g., mounted outside or inside a housing 104, as shown in FIG. 3).

In some embodiments, the processor(s) 130 can be used to control subsequent NMR data acquisition activities (after the preferred NMR frequency is determined). Thus, the apparatus 100 may comprise a telemetry transmitter (e.g., as part of the transceiver 144) to communicate NMR data to a surface logging facility 156, wherein the processor 130 is configured to control generation of the pulse train 212 using the preferred NMR frequency 232, and to control acquisition of the NMR data responsive to the preferred NMR frequency 232 after the preferred NMR frequency 232 is determined.

Some embodiments include a variety of ex-situ systems 164. For example, a system 164 to locate the preferred NMR frequency may comprise a housing 104, at least one electromagnetic transmitter and receiver pair (T, R) attached to the housing 104, and one or more processors 130 attached to the housing 104. The housing 104 may comprise a down hole tool, such as a wireline tool or a measurement while drilling (MWD) tool.

As part of the system 164, additional processors 130, perhaps located on the surface 166, may be used to generate images 118 for storage and display. Thus, the system 164 may comprise a second processor 130 (e.g., in the workstation of the logging facility 156) to generate an image 118 based on data 170 acquired by a first processor 130 (e.g., included down hole in the apparatus 100) using the preferred NMR frequency 232.

A memory 150 can be located in the housing 104 to store data 170, including images 118. For example, the data 170 and images 118 may be stored in a database 134. Additional embodiments may be realized, and thus, additional examples of system embodiments will now be described.

Figure 4:
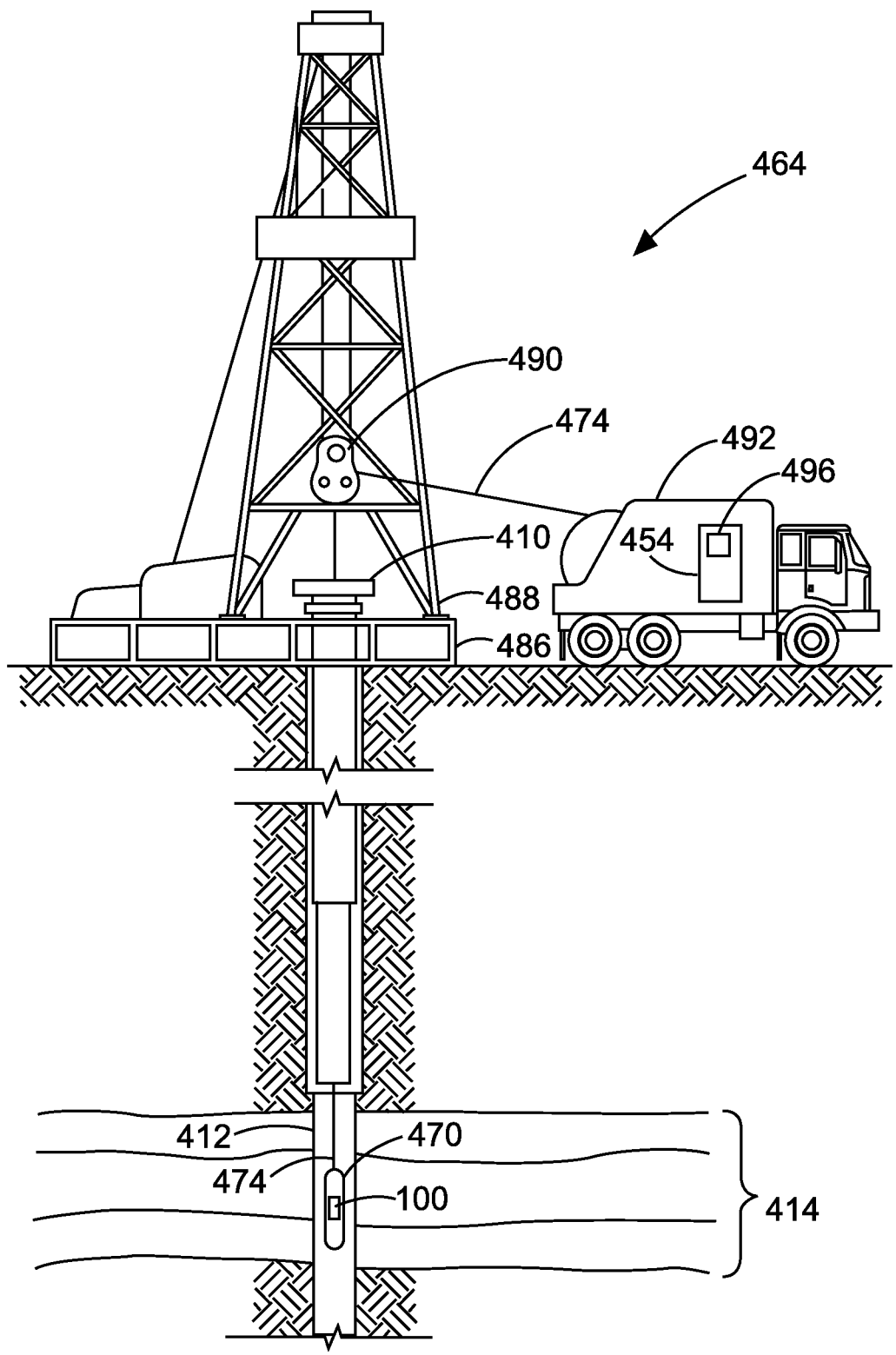
FIG. 4 illustrates an ex-situ wireline system embodiment of the invention.
Figure 5:
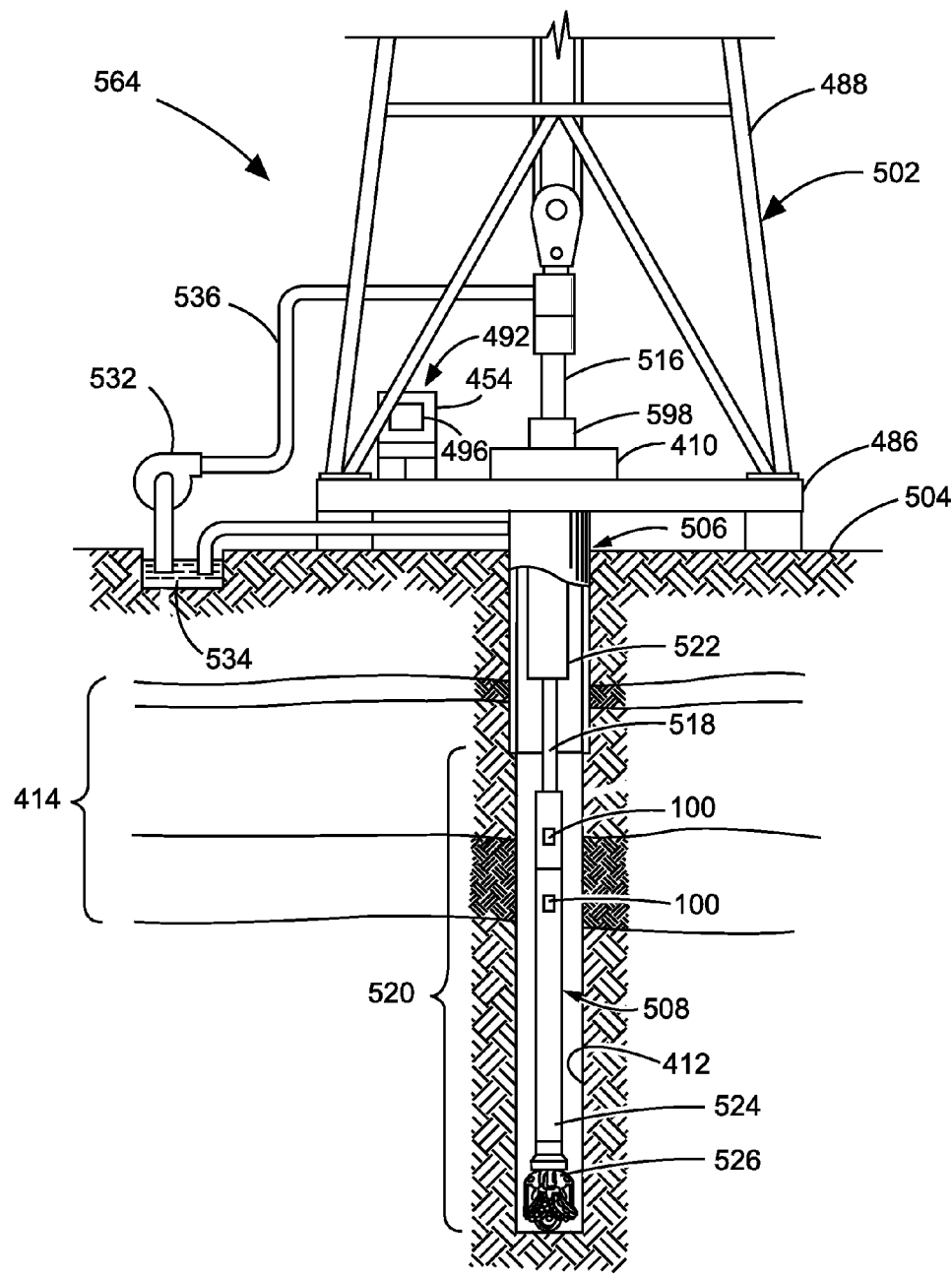
FIG. 5 illustrates an ex-situ drilling rig system embodiment of the invention.

FIG. 4 illustrates an ex-situ wireline system 464 embodiment of the invention, and FIG. 5 illustrates an ex-situ drilling rig system 564 embodiment of the invention. Therefore, the systems 464, 564 may comprise portions of a wireline logging tool body 470 as part of a wireline logging operation, or of a down hole tool 524 as part of a down hole drilling operation.

Thus, FIG. 4 shows a well during wireline logging operations. In this case, a drilling platform 486 is equipped with a derrick 488 that supports a hoist 490.

Drilling oil and gas wells is commonly carried out using a string of drill pipes connected together so as to form a drilling string that is lowered through a rotary table 410 into a wellbore or borehole 412. Here it is assumed that the drilling string has been temporarily removed from the borehole 412 to allow a wireline logging tool body 470, such as a probe or sonde, to be lowered by wireline or logging cable 474 into the borehole 412. Typically, the wireline logging tool body 470 is lowered to the bottom of the region of interest and subsequently pulled upward at a substantially constant speed.

During the upward trip, at a series of depths various instruments (e.g., portions of the apparatus 100, or system 164 shown in FIG. 1) included in the tool body 470 may be used to perform measurements on the subsurface geological formations 414 adjacent the borehole 412 (and the tool body 470). The measurement data can be communicated to a surface logging facility 492 for processing, analysis, and/or storage. The logging facility 492 may be provided with electronic equipment for various types of signal processing, which may be implemented by any one or more of the components of the apparatus 100 or system 164 in FIG. 1. Similar formation evaluation data may be gathered and analyzed during drilling operations (e.g., during LWD operations, and by extension, sampling while drilling).

In some embodiments, the tool body 470 is suspended in the wellbore by a wireline cable 474 that connects the tool to a surface control unit (e.g., comprising a workstation 454). The tool may be deployed in the borehole 412 on coiled tubing, jointed drill pipe, hard wired drill pipe, or any other suitable deployment technique.

Turning now to FIG. 5, it can be seen how a system 564 may also form a portion of a drilling rig 502 located at the surface 504 of a well 506. The drilling rig 502 may provide support for a drill string 508. The drill string 508 may operate to penetrate the rotary table 410 for drilling the borehole 412 through the subsurface formations 414. The drill string 508 may include a Kelly 516, drill pipe 518, and a bottom hole assembly 520, perhaps located at the lower portion of the drill pipe 518.

The bottom hole assembly 520 may include drill collars 522, a down hole tool 524, and a drill bit 526. The drill bit 526 may operate to create the borehole 412 by penetrating the surface 504 and the subsurface formations 414. The down hole tool 524 may comprise any of a number of different types of tools including MWD tools, LWD tools, and others.

During drilling operations, the drill string 508 (perhaps including the Kelly 516, the drill pipe 518, and the bottom hole assembly 520) may be rotated by the rotary table 410. Although not shown, in addition to, or alternatively, the bottom hole assembly 520 may also be rotated by a motor (e.g., a mud motor) that is located down hole. The drill collars 522 may be used to add weight to the drill bit 526. The drill collars 522 may also operate to stiffen the bottom hole assembly 520, allowing the bottom hole assembly 520 to transfer the added weight to the drill bit 526, and in turn, to assist the drill bit 526 in penetrating the surface 504 and subsurface formations 414.

During drilling operations, a mud pump 532 may pump drilling fluid (sometimes known by those of ordinary skill in the art as "drilling mud") from a mud pit 534 through a hose 536 into the drill pipe 518 and down to the drill bit 526. The drilling fluid can flow out from the drill bit 526 and be returned to the surface 504 through an annular area 540 between the drill pipe 518 and the sides of the borehole 412. The drilling fluid may then be returned to the mud pit 534, where such fluid is filtered. In some embodiments, the drilling fluid can be used to cool the drill bit 526, as well as to provide lubrication for the drill bit 526 during drilling operations. Additionally, the drilling fluid may be used to remove subsurface formation cuttings created by operating the drill bit 526.

Thus, referring now to FIGS. 1-5, it may be seen that in some embodiments, systems 164, 464, 564 may include a drill collar 522, a down hole tool 524, and/or a wireline logging tool body 470 to house one or more apparatus 100, similar to or identical to the apparatus 100 described above and illustrated in FIGS. 1 and 3. Components of the system 164 in FIG. 1 may also be housed by the tool 524 or the tool body 470.

Thus, for the purposes of this document, the term "housing" may include any one or more of a drill collar 522, a down hole tool 524, or a wireline logging tool body 470 (all having an outer surface and an inner surface, used to enclose or attach to magnetometers, sensors, fluid sampling devices, pressure measurement devices, temperature measurement devices, transmitters, receivers, acquisition and processing logic, and data acquisition systems). The down hole tool 524 may comprise a logging while drilling (LWD) tool, or an MWD tool. The wireline tool body 470 may comprise a wireline logging tool, including a probe or sonde, for example, coupled to a logging cable 474. Many embodiments may thus be realized.

For example, in some embodiments, a system 464, 564 may include a display 496 to present NMR data, both as measured and as processed/calculated, as well as database information, perhaps in graphic form. A system 464, 564 may also include computation logic, perhaps as part of a surface logging facility 492, or a computer workstation 454, to receive signals from transmitters and to send signals to receivers, and other instrumentation, to determine properties of the formation 414.

Thus, a system 464, 564 may comprise a down hole tool body, such as a wireline logging tool body 470 or a down hole tool 524 (e.g., an LWD or MWD tool body), and portions of one or more apparatus 100 attached to the tool body, the apparatus 100 to be constructed and operated as described previously. The processor(s) 130 in the systems 464, 564 may be attached to the housing 104, or located at the surface, as part of a surface computer (e.g., in the surface logging facility 156) as shown in FIG. 1.

The apparatus 100; housing 104; field 112; formations 114, 414; images 118; data acquisition system 124; processor(s) 130; database 134; logic 140; transceiver 144; memory 150; logging facilities 156, 492; systems 164, 464, 564; surface 166; data 170; process 211; pulse train 212; pulses 214, 216; echo acquisition period 218; REFID signal 220; transformation 224; decomposed frequency components 228; preferred NMR frequency 232; graph 240; chassis 340; rotary table 410; borehole 412; computer workstations 454; wireline logging tool body 470; logging cable 474; drilling platform 486; derrick 488; hoist 490; logging facility 492; display 496; drill string 508; Kelly 516; drill pipe 518; bottom hole assembly 520; drill collars 522; down hole tool 524; drill bit 526; mud pump 532; mud pit 534; hose 536; receiver(s) R; and transmitters (s) T may all be characterized as "modules" herein.

Such modules may include hardware circuitry, and/or a processor and/or memory circuits, software program modules and objects, and/or firmware, and combinations thereof, as desired by the architect of the apparatus 100 and systems 164, 464, 564 and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of apparatus 100 and systems 164, 464, 564 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules. Such apparatus and systems may further be included as sub-components within a variety of electronic systems, such as televisions, cellular telephones, personal computers, workstations, radios, video players, vehicles, signal processing for geothermal tools and smart transducer interface node telemetry systems, among others. Some embodiments include a number of methods.

Figure 6:
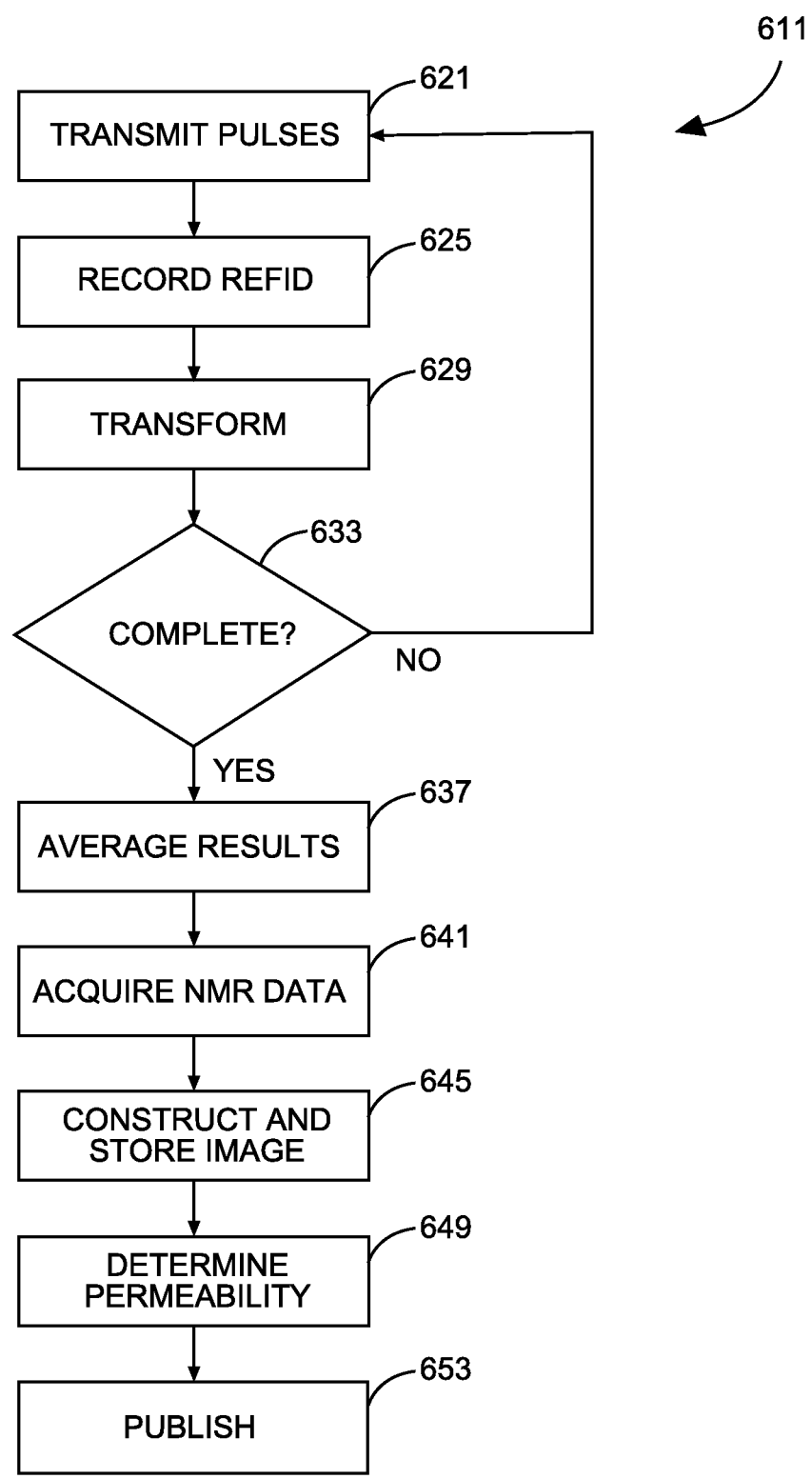
FIG. 6 is a flow chart illustrating several methods according to various embodiments of the invention.

For example, FIG. 6 is a flow chart illustrating several ex-situ NMR methods 611 according to various embodiments of the invention. One example of using the method 611 may comprise operating an ex-situ apparatus or system to transmit a train of modulated pulses, to acquire and record the resulting REFID signals, and to transform the acquired REFID signals to determine a preferred NMR frequency. The preferred NMR frequency, which comprises one of several potential operational frequencies, often provides the best signal-to-noise ratio for the acquired REFID signals during the echo acquisition period that follows each of the pulses in the train provided by the transmitter.

Thus, a processor-implemented, ex-situ NMR method 611, to execute on one or more processors that perform the method 611, may begin at block 621 with transmitting first and second modulated pulses to generate an externally-projected oscillating magnetic field in a material body, such as a geological formation or a human body. The first and second modulated pulses may be followed by a series of the second modulated pulses. Any one or more of the first and second modulated pulses may comprise a "wideband" pulse, defined for the purposes of this document as having a bandwidth greater than or equal to three percent of the pulse center transmit frequency.

In some embodiments, chirp pulses can be used in place of either of the first or second pulses, or both. Thus, at least one of the first or the second modulated pulses may comprise a chirp pulse.

In some embodiments, the first modulated pulse may comprise a $\pi/2$ pulse. In some embodiments, the second modulated pulses may comprise $\pi$ pulses.

In some embodiments, phase modulation or frequency modulation can be used to form the pulses. Thus, one or more of the first or the second modulated pulses may comprise a phase-modulated pulse. Similarly, one or more of the first or the second modulated pulses may comprise a frequency-modulated pulse.

In some embodiments, amplitude modulation can be used to form the pulses. Thus, one or more of the first or the second modulated pulses may comprise an amplitude-modulated pulse.

The method 611 may continue on to block 625 with recording at least one REFID signal during an echo acquisition period that follows each of the first and/or the second modulated pulses.

The method 611 may continue on to block 629 with transforming one of more of the acquired REFID signals via frequency decomposition into decomposed frequency components to determine a preferred NMR frequency. The preferred NMR frequency may be selected for the material body (e.g., a geological formation) and the current temperature surrounding the magnet that cooperates with the transmitter and the receiver to provide the REFID signal as a frequency associated with one of the decomposed frequency components having the maximum amplitude. The activity at block 629 may comprise applying an FFT to the REFID to produce the decomposed frequency components as transformation results.

If the acquisition of REFID signals is not complete, as determined at block 633, the method 611 may return to block 621. Otherwise, the method 611 may continue on to block 637. For example, additional pulses in the train may be generated, with a bandwidth of the first and/or second pulses that is incrementally increased over several pulse-echo acquisition cycles. Thus, the method 611 may comprise repeating the transmitting, the recording, and the transforming (at blocks 621, 625, 629, respectively) using progressively larger ranges of frequency as the bandwidth for the pulses in the train provided by the transmitter.

In some embodiments, the decomposed frequency components can be averaged over several echo acquisition periods. Averaging may occur prior to the transformation at block 629, or afterwards. Thus, the method 611 may continue on to block 637 to include averaging the transformation results over multiple ones of the echo acquisition periods.

In most embodiments, after the preferred NMR frequency is determined, the preferred NMR frequency can be used to generate NMR data, which is used in turn to construct spectra that can be used to predict characteristics of the material body, such as a geological formation (e.g., the oil-gas-water ratio). Thus, the method 611 may continue on to block 641 with acquiring NMR data using the preferred NMR frequency, and to block 645 with constructing and storing spectra of the material body (e.g., a geological formation) in a memory, the spectra constructed using the NMR data. The spectra, such as T2, T1, T2–T1, and/or T2–D spectra, is a graph or some other image. The information in the image may provide characteristics of the material body, such as the oil-gas-water ratio for a geological formation.

In some embodiments then, the preferred NMR frequency can be used (indirectly) to generate an image, such as a map of formation permeability. Images can be displayed immediately, or stored for display at a later time. Thus, when the material body comprises a geological formation, the method 611 may continue on to block 649 with determining permeability of the formation based on the preferred NMR frequency, and to block 653 with publishing a map of the permeability on a display.

It should be noted that the processes and methods described herein do not have to be executed in the order described, or in any particular order. Moreover, various activities described with respect to the processes and methods identified herein can be executed in iterative, serial, or parallel fashion. The various elements of each process and method (e.g., the processes shown in FIG. 2, and the methods shown in FIG. 6) can be substituted, one for another, within and between the processes and methods. Information, including parameters, commands, operands, and other data, can be sent and received in the form of one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand the various programming languages that may be employed to create one or more software programs designed to implement and perform the methods disclosed herein. For example, the programs may be structured in an object-orientated format using an object-oriented language such as Java or C#. In another example, the programs can be structured in a procedure-orientated format using a procedural language, such as assembly or C or hardware description language, such as VHDL. The software components may communicate using any of a number of mechanisms well known to those skilled in the art, such as application program interfaces or interprocess communication techniques, including remote procedure calls. The teachings of various embodiments are not limited to any particular programming language or environment. Thus, other embodiments may be realized.

Figure 7:
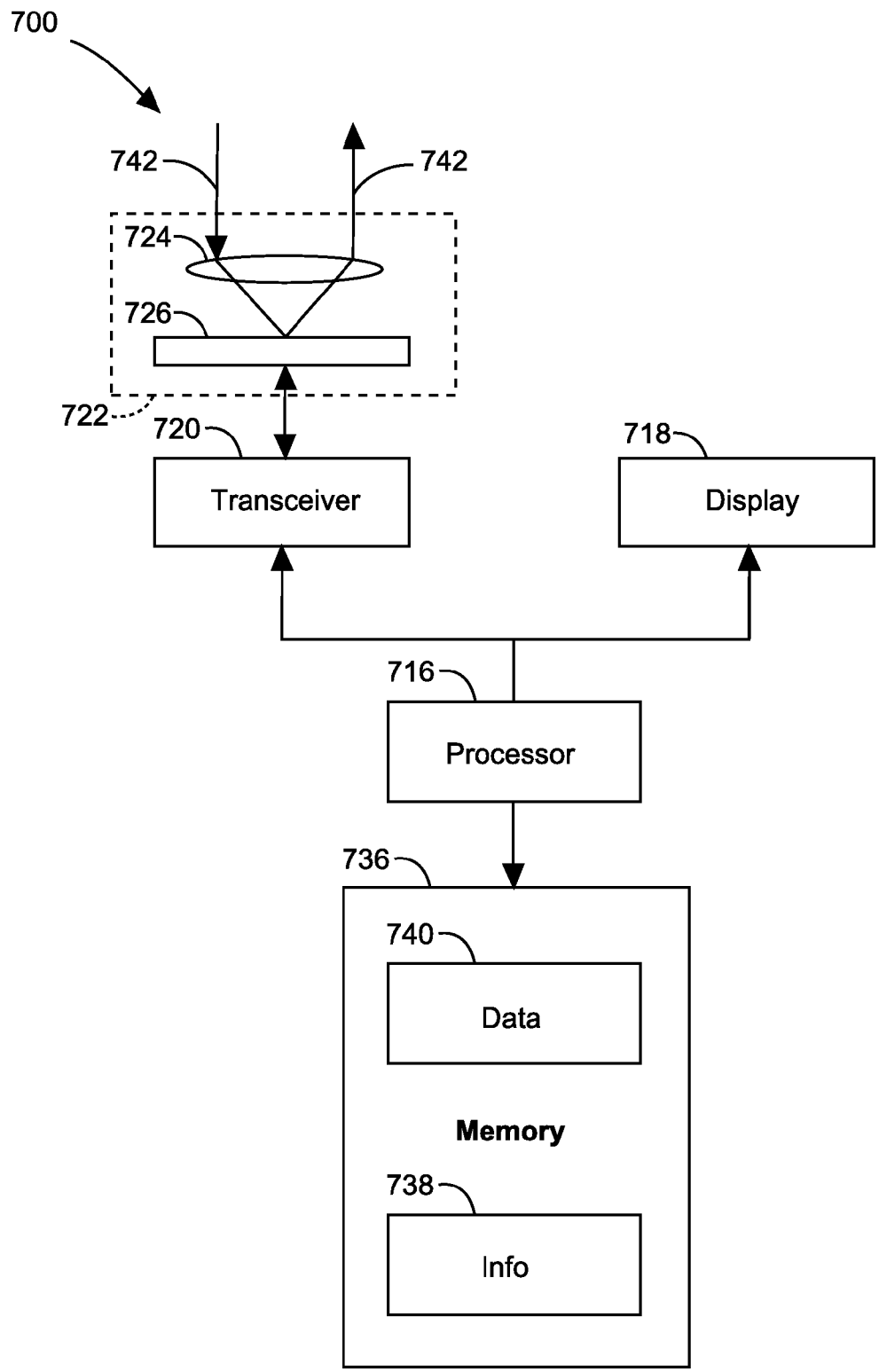
FIG. 7 is a block diagram of an article according to various embodiments of the invention.

For example, FIG. 7 is a block diagram of an article 700 of manufacture according to various embodiments, such as a computer, a memory system, a magnetic or optical disk, or some other storage device. The article 700 may include one or more processors 716 coupled to a machine-accessible medium such as a memory 736 (e.g., removable storage media, as well as any tangible, non-transitory memory including an electrical, optical, or electromagnetic conductor) having associated information 738 (e.g., computer program instructions and/or data), which when executed by one or more of the processors 716, results in a machine (e.g., the article 700) performing any actions described with respect to the processes of FIG. 2, the methods of FIG. 6, the apparatus of FIG. 1, and the systems of FIGS. 1, 4, and 5. The processors 716 may comprise one or more processors sold by Intel Corporation (e.g., Intel® Core™ processor family), Advanced Micro Devices (e.g., AMD Athlon™ processors), and other semiconductor manufacturers.

In some embodiments, the article 700 may comprise one or more processors 716 coupled to a display 718 to display data processed by the processor 716 and/or a wireless transceiver 720 (e.g., a down hole telemetry transceiver) to receive and transmit data processed by the processor.

The memory system(s) included in the article 700 may include memory 736 comprising volatile memory (e.g., dynamic random access memory) and/or non-volatile memory. The memory 736 may be used to store data 740 processed by the processor 716.

In various embodiments, the article 700 may comprise communication apparatus 722, which may in turn include amplifiers 726 (e.g., preamplifiers or power amplifiers) and one or more antenna 724 (e.g., transmitting antennas and/or receiving antennas). Signals 742 received or transmitted by the communication apparatus 722 may be processed according to the methods described herein.

Many variations of the article 700 are possible. For example, in various embodiments, the article 700 may comprise a down hole tool, including the apparatus 100 shown in FIG. 1. In some embodiments, the article 700 is similar to or identical to the apparatus 100 or system 164 shown in FIG. 1.

In summary, the apparatus, systems, and methods disclosed herein may provide a searching mechanism that can be used to determine a preferred NMR frequency (e.g., one that provides a maximal or maximum SNR in the acquired REFID signal) relatively rapidly, in a laboratory or down hole, so that an oven may not be needed to maintain magnet temperature over longer periods of time. As the result, in the petrochemical arena, the production process may be shortened, and the value of the services provided by an operation/exploration company that implements this mechanism may be significantly enhanced.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An ex-situ nuclear magnetic resonance (NMR) apparatus, comprising:
   at least one electromagnetic transmitter and receiver pair; and
   a first processor to record at least one raw echo free induction decay (REFID) signal provided by the receiver during an echo acquisition period that follows each of a series of second modulated pulses forming part of a pulse train transmitted by the transmitter, the pulse train comprising a first modulated pulse followed by the series of the second modulated pulses, the pulse train to generate an externally-projected oscillating magnetic field in a material body, wherein both the first and the second modulated pulses have a bandwidth greater than three percent of their center transmit frequency, and wherein the first processor is to transform the at least one of the REFID signals via frequency decomposition into decomposed frequency components to determine a preferred NMR frequency for the at least one electromagnetic transmitter and receiver pair associated with one of the decomposed frequency components having a maximum amplitude.

2. The apparatus of claim 1, wherein the at least one electromagnetic transmitter and receiver pair, and the first processor, are attached to a common chassis.

3. The apparatus of claim 1, further comprising:
   a telemetry transmitter to communicate NMR data to a surface logging facility, wherein the first processor is configured to control generation of the pulse train using the preferred NMR frequency, and to control acquisition of the NMR data responsive to the preferred NMR frequency after the preferred NMR frequency is determined.

4. The apparatus of claim 1, wherein the material body comprises a geological formation.

5. The apparatus of claim 4, further comprising:
   a housing attached to the at least one electromagnetic transmitter and receiver pair and the first processor.

6. The apparatus of claim 5, wherein the housing comprises one of a wireline tool or a measurement while drilling tool.

7. The apparatus of claim 5, further comprising:
   a second processor to generate an image based on data acquired by the first processor using the preferred NMR frequency.

8. A processor-implemented, ex-situ nuclear magnetic resonance (NMR) method, to execute on one or more processors that perform the method, comprising:
   transmitting first and second modulated pulses to generate an externally-projected oscillating magnetic field in a material body, followed by a series of the second modulated pulses, wherein the second modulated pulses have a bandwidth greater than three percent of their center transmit frequency;
   recording at least one raw echo free induction decay (REFID) signal during an echo acquisition period that follows each of the second modulated pulses; and
   transforming the at least one of the REFID signals via frequency decomposition into decomposed frequency components to determine a preferred NMR frequency for at least one electromagnetic transmitter and receiver pair associated with one of the decomposed frequency components having a maximum amplitude.

9. The method of claim 8, wherein the transforming comprises:
   applying a fast Fourier transform (FFT) to the REFID to produce the decomposed frequency components as transformation results.

10. The method of claim 9, wherein the transforming comprises:
    applying a series of quadrature filters to generate the decomposed frequency components as the transformation results.

11. The method claim 9, further comprising:
    averaging the transformation results over multiple ones of the echo acquisition periods.

12. The method claim 8, further comprising:
    repeating the transmitting, the recording, and the transforming using progressively larger ranges of frequency as the bandwidth.

13. The method of claim 8, wherein at least one of the first or the second modulated pulses comprises a chirp pulse.

14. The method of claim 8, wherein the first modulated pulse comprises a π/2 pulse.

15. The method of claim 8, wherein the second modulated pulses comprise π pulses.

16. The method of claim 8, wherein at least one of the first or the second modulated pulses comprise a phase-modulated pulse.

17. The method of claim 8, wherein at least one of the first or the second modulated pulses comprise a frequency-modulated pulse.

18. The method of claim 8, wherein at least one of the first or the second modulated pulses comprise an amplitude-modulated pulse.

19. The method of claim 8, further comprising:
    determining permeability of the material body as a geological formation based on the preferred NMR frequency; and
    publishing a map of the permeability on a display.

20. An article including a non-transitory machine-accessible medium having instructions stored therein, wherein the instructions, when accessed, result in a machine performing an ex-situ, nuclear magnetic resonance (NMR) method comprising:
- transmitting first and second modulated pulses to generate an externally-projected oscillating magnetic field into a material body, followed by a series of the second modulated pulses, wherein the second modulated pulses have a bandwidth greater than three percent of their center transmit frequency;
- recording at least one raw echo free induction decay (REFID) signal during an echo acquisition period that follows each of the second modulated pulses; and
- transforming the at least one of the REFID signals via frequency decomposition into decomposed frequency components to determine a preferred NMR frequency for at least one electromagnetic transmitter and receiver pair associated with one of the decomposed frequency components having a maximum amplitude.

21. The article of claim 20, wherein the instructions, when accessed, result in the machine performing:
- acquiring NMR data using the preferred NMR frequency;
- storing spectra derived from the NMR data in a memory; and
- constructing an image from the spectra.

22. The article of claim 21, wherein the instructions, when accessed, result in the machine performing:
- publishing the image to a display.

\* \* \* \* \*